US009057081B2

(12) United States Patent
Hutcheson et al.

(10) Patent No.: US 9,057,081 B2
(45) Date of Patent: Jun. 16, 2015

(54) **CARBOHYDRASE EXPRESSION DURING DEGRADATION OF WHOLE PLANT MATERIAL BY *SACCHAROPHAGUS DEGRADANS***

(75) Inventors: Steven Hutcheson, Columbia, MD (US); Ronald Weiner, Potomac, MD (US)

(73) Assignee: Aemetis Technologies, Inc., Cupertino, CA (US)

( * ) Notice: Subject to any disclaimer, the term of this patent is extended or adjusted under 35 U.S.C. 154(b) by 1405 days.

(21) Appl. No.: 12/112,776

(22) Filed: Apr. 30, 2008

(65) Prior Publication Data

US 2009/0117619 A1    May 7, 2009

Related U.S. Application Data

(60) Provisional application No. 60/914,936, filed on Apr. 30, 2007.

(51) Int. Cl.
*C12N 9/42* (2006.01)
*C12P 7/10* (2006.01)
*C12P 7/14* (2006.01)
*C12P 19/02* (2006.01)

(52) U.S. Cl.
CPC .............. *C12P 7/10* (2013.01); *C12N 9/2434* (2013.01); *C12P 7/14* (2013.01); *C12P 19/02* (2013.01); *Y02E 50/16* (2013.01); *Y02E 50/17* (2013.01); *C12N 9/2437* (2013.01)

(58) Field of Classification Search
CPC .................................... C12N 9/42; C12N 1/20
See application file for complete search history.

(56) References Cited

U.S. PATENT DOCUMENTS

| | | | | |
|---|---|---|---|---|
| 6,759,040 | B1 * | 7/2004 | Manyak et al. | 424/94.2 |
| 7,365,180 | B2 * | 4/2008 | Taylor et al. | 536/23.1 |
| 2006/0105914 | A1 * | 5/2006 | Taylor et al. | 504/117 |
| 2006/0128946 | A1 | 6/2006 | Weiner et al. | |
| 2007/0292929 | A1 | 12/2007 | Weiner et al. | |
| 2008/0293115 | A1 | 11/2008 | Taylor et al. | |

FOREIGN PATENT DOCUMENTS

| WO | 99/14312 A | 3/1999 |
|---|---|---|
| WO | 2008136997 A2 | 11/2008 |

OTHER PUBLICATIONS

Taylor et al., 2006, Complete Cellulase System in the Marine Bacterium *Saccharophagus degradans* Strain 2-40 T, Journal of Bacteriology, 188(11): 3849-3861.*
Bhat, Cellulases and Related Enzymes in Biotechnology, (2000), Biotech. Advances, 18(5):355-383.
Supplemental European Search Report, Application No. EP08754151.2, Date Mailed: May 5, 2009, See note in Office action.
Aristidou et al. (2000), "Metabolic engineering applications to renewable resource utilization," Curr. Opin. in Biotechnol., 11:187-198.
De Carvalho Lima et al. (2002), "Ethanol production from corn cob hydrolysates by *Escherichia coli* LO11," J. Ind. Micobiol. Biotechnol., 29:124-128.
Ekborg et al. (2005), "*Saccharophagus degradans* gen. nov., sp. nov., a versatile marine degrader complex polysaccharides," Int. J. Syst. and Evolu. Microbiol., 55:1545-1549.
Emami et al. (2002), "Evidence for temporal regulation of the two *Pseudomonas cellulosa* xylanases belong to glycoside hydrolase family 11," J. Bact., 184:4124-4133.
International Search Report for PCT/US2008/005559, mailed Oct. 28, 2008, see note in Office action.
Klinke et al. (2004), "Inhibition of ethanol-producing yeast and bacteria by degradation products produced during pretreatment of biomass," Appl. Micro. Biotechnol., 66:10-26.
Lin et al. (2006), "Ethanol fermentation from biomass resources: current stat and prospects," Appl Microbiol Biotechnol., 69:627-642.
Taylor et al. (2006), "Complete cellulase system in the marine bacterium *Saccharophagus degradans* strain 2-40T," J. Bact., 188:3849-3861.
Tolan, (2002) "Logen's process for producing ethanol from cellulosic biomass," Clean Tech. Env. Policy, 3:339-345.
Zverlov et al. (2002), "A newly described cellulosomal cellobiohydrolasse, Celo. from *Clostridium thermocellum*: investigation of the exo-mode of hydrolysis, and binding capacity to crystalline cellulose," Microbiology, 148:247-255.
Kyslikova et al., "Cell growth and cellulase production in trichoderma viride on microcrystalline cellulose", Folia Microbiol. (1981), 26:303-308.
Canadian Office Action, Application No. CA 2,685,864, Dated: Mar. 5, 2010, See note in Office action.
Andrykovitch G. et al., "Isolation of a New Polysaccharide-Digesting Bacterium from a Salt Marsh." Appl. and Environmental Microbiol. (1998), 54(4):1061-62.
Examination Report, Application No. EP 08754151.2, Mailed on: May 12, 2010, See note in Office action.
Coutinho P.M. et al., "The Modular Structure of Cellulases and Other Carbohydrate-Active Enzymes: An Integrated Database Approach." Genetics, Biochemistry and Ecology of Cellulose Degradation. (1999), T. Kimura, Tokyo University Publishers Co: 15-23.
Dien B.S. et al., "Development of New Ethanologenic *Escherichia coli* Strains for Fermentation of Lignocellulosic Biomass." Appl. Biochem. and Biotech. (2000), 84-86:181-96.
Ensor L.A. et al., "Expression of Multiple Complex Polysaccharide-Degrading Enzyme Systems by Marine Bacterium Strain 2-40." J. Indust. Microbiol. & Biotech. (1999), 23:123-26.

(Continued)

*Primary Examiner* — Allison Fox
(74) *Attorney, Agent, or Firm* — Lathrop & Gage LLP

(57) ABSTRACT

The present invention relates to cell wall degradative systems, in particular to systems containing enzymes that bind to and/or depolymerize cellulose, hemicellulose and other carbohydrates. These systems have a number of applications.

13 Claims, 6 Drawing Sheets

(56) References Cited

OTHER PUBLICATIONS

Gonzalez J.M. et al., "Phylogenetic Characterization of Marine Bacterium Strain 2-40, a Degrader of Complex Polysaccharides." Int. J. of Systematic and Evolutionary Microbiology, (2000), 8:831-34.

Henrissat B. et al., "A Scheme for Designating Enzymes that Hydrolyse the Polysaccharides in the Cell Walls of Plants." FEBS Lett., (1998), 425:352-54.

Henrissat B. et al., "New Families in the Classification of Glycosyl Hydrolases Based on Amino Acid Sequence Similarities." Biochem. J., (1993), 293:781-788.

Warren R.A.J., "Microbial Hydrolysis of Polysaccharides." Annu. Rev. Microbiol. (1996), 50:183-212.

Whitehead L.A. et al., "Characterization of the Agarase System of a Multiple Carbohydrate Degrading Marine Bacterium." Cytobios, (2001), 106(S1):99-117.

ATCC No. 43961, [online]. [Retrieved on Feb. 12, 2012] Retrieved from http://www.atcc.org/ATCCAdvancedCatalogSearch/ProductDetails/tabid/452.

COG3693: Beta-1,4-xylanse [*Microbulbifer degradans* 2-40] NCBI Reference: ZP_000666395.1 [online]. [Retrieved on Feb. 21, 2012] Retrieved from: http://www.ncbi.nim.nih.gov/protein/ZP_00066395.1.

Q21PD4, Putative xylanase [online]. [Retrieved on Feb. 21, 2012] Retrieved from: http://www.uniprot.org/uniprot/Q21PD4.

Q21EL2, Putative bifunctional xylanase/a-L-arabinofuranosidase [online]. [Retrieved on Feb. 21, 2012] Retrieved from: http://www.uniprot.org/uniprot/Q21EL2.

Q21G18, MCP methyltransferase, CheR-type [online]. [Retrieved on Feb. 21, 2012] Retrieved from: http://www.uniprot.org/uniprot/Q21G18.

Q21HD6, Putative xylanase [online]. [Retrieved on Feb. 21, 2012] Retrieved from: http://www.uniprot.org/uniprot/Q21HD6.

Q21NZ2, Xylanase-like protein [online]. [Retrieved on Feb. 21, 2012] Retrieved from: http://www.uniprot.org/uniprot/Q21NZ2.

COG2730: Endoglucanase [Microfulbifer degradans 2-40] [online]. [Retrieved on Feb. 21, 2012] Retrieved from: http://www.ncbi.nim.nih.gov/protein/ZP_00066178.1.

Glick et al, "Isolation, Characterization and Manipulation of Cellulase Genes", Biotech. Adv., vol. 7, pp. 361-386, 1989.

Krishna, S. Hari, et al. "Simultaneous saccharification and fermentation of lignocellulosic wastes to ethanol using a thermotolerant yeast." Bioresource Technology, 77:193-196 (2001).

Taylor, Larry E., II. "Degradation of Plant Cell Wall Polysaccharides by *Saccharophgus degradans*", Doctor of Philosophy Dissertation, Graduate School of the University of Maryland (2005).

Zhang, H., et al. "Carbohydrase expression during degradation of whole plant material by *Saccharophagus degradans*." Poster Session 1, 1B-43, 29th Symposium on Biotechnology for Fuels and Chemicals, Apr. 29, 2007, Denver, Colorado.

* cited by examiner

US 9,057,081 B2

CARBOHYDRASE EXPRESSION DURING DEGRADATION OF WHOLE PLANT MATERIAL BY *SACCHAROPHAGUS DEGRADANS*

RELATED APPLICATIONS

This application claims priority of U.S. Provisional Application No. 60/914,936, filed on Apr. 30, 2007 and incorporated herein by reference in its entirety.

BACKGROUND OF THE INVENTION

*Saccharophagus degradans* strain 2-40 (herein referred to as "*S. degradans* 2-40") is a representative of an emerging group of marine bacteria that degrade complex polysaccharides (CP). *S. degradans* has been deposited at the American Type Culture Collection and bears accession number ATCC 43961. *S. degradans* 2-40 is a marine γ-proteobacterium that was isolated from decaying *Spartina alterniflora*, a salt marsh cord grass in the Chesapeake Bay watershed. Consistent with its isolation from decaying plant matter, *S. degradans* strain 2-40 is able to degrade many complex polysaccharides, including cellulose, pectin, xylan, and chitin, which are common components of the cell walls of higher plants. *S. degradans* strain 2-40 is also able to depolymerize algal cell wall components, such as agar, agarose, and laminarin, as well as protein, starch, pullulan, and alginic acid. In addition to degrading this plethora of polymers, *S. degradans* strain 2-40 can utilize each of the polysaccharides as the sole carbon source. Therefore, *S. degradans* strain 2-40 is not only an excellent model of microbial degradation of insoluble complex polysaccharides (ICPs) but can also be used as a paradigm for complete metabolism of these ICPS. ICPs are polymerized saccharides that are used for form and structure in animals and plants. They are insoluble in water and therefore are difficult to break down.

*S. degradans* strain 2-40 requires at least 1% sea salts for growth and will tolerate salt concentrations as high as 10%. It is a highly pleomorphic, Gram-negative bacterium that is aerobic, generally rod-shaped, and motile by means of a single polar flagellum. Previous work has determined that 2-40 can degrade at least 10 different carbohydrate polymers (CP), including agar, chitin, alginic acid, carboxymethylcellulose (CMC), β-glucan, laminarin, pectin, pullulan, starch and xylan. In addition, it has been shown to synthesize a true tyrosinase. 16S rDNA analysis shows that 2-40 is a member of the gamma-subclass of the phylum Proteobacteria, related to *Microbulbifer hydrolyticus* and to *Teridinobacter* sp., cellulolytic nitrogen-fixing bacteria that are symbionts of shipworms.

The agarase, chitinase and alginase systems have been generally characterized. Zymogram activity gels indicate that all three systems are comprised of multiple depolymerases and multiple lines of evidence suggest that at least some of these depolymerases are attached to the cell surface. Activity assays reveal that the majority of *S. degradans* enzyme activity resides with the cell fraction during logarithmic growth on CP, while in later growth phases the bulk of the activity is found in the supernatant and cell-bound activity decreases dramatically (Stotz 1994). Growth on CP is also accompanied by dramatic alterations in cell morphology. Glucose-grown cultures of *S. degradans* are relatively uniform in cell size and shape, with generally smooth and featureless cell surfaces. However, when grown on agarose, alginate, or chitin, *S. degradans* cells exhibit novel surface structures and features.

There exists a need to identify enzyme systems that use cellulose as a substrate, express the genes encoding the proteins using suitable vectors, identify and isolate the amino acid products (enzymes and non-enzymatic products), and use these products as well as organisms containing these genes for purposes such as ethanol production.

SUMMARY OF THE INVENTION

The invention provides a method for creating a mixture of enzymes for the degradation of plant material. Preferably, this degradation occurs without chemical pretreatments of the plant material. This method comprises growing *Saccharophagus degradans* in the presence of a given plant material and then measuring the expression of enzymes that are expressed in the *Saccharophagus degradans*. The enzymes that undergo increased expression in the presence of the given plant material are combined to form a mixture of enzymes for the degradation of the given plant material.

The invention also provides a modified bacterium in which enzymes that are upregulated in *Saccharophagus degradans* in the presence of a given plant material are constitutively expressed at an increased rate of expression. The modified bacterium is able to degrade the given plant material at a much faster rate than a non-modified bacterium.

The invention also provides a method of producing ethanol, wherein a bacterium is used to degrade one or more plant materials, and the simpler sugars that result from the degradation process are used to produce ethanol in an aqueous mixture with the one or more plant materials. The ethanol is produced by any way known in the art. In one embodiment, the ethanol is produced from the degradation product of the bacterium by a yeast cell. The bacterium may be *Saccharophagus degradans* strain 2-40 or it may be a modified bacterium that expresses enzymes upregulated in *Saccharophagus degradans* in response to the presence of the given plant material. In specific embodiments of the invention the aqueous mixture of bacteria and one or more plant materials comprises at least 1% salt and/or at most 10% salt. These embodiments of the invention are also used to make sugar by omitting steps to convert sugars to ethanol.

The invention also provides a method of producing ethanol, wherein a mix of enzymes is used to degrade a given plant material, and the simpler sugars that result from the degradation process are used to produce ethanol. The ethanol is produced by any way known in the art. In one embodiment, the ethanol is produced from the degradation product of the bacterium by a yeast cell. The mix of enzymes is two or more of the enzymes upregulated in *Saccharophagus degradans* strain 2-40 in response to the presence of the given plant material. The enzymes are harvested from the *Saccharophagus degradans* strain 2-40 by any method known in the art. In specific embodiments of the invention the aqueous mixture of proteins and one or more plant materials comprises at least 1% salt and/or at most 10% salt. In other specific embodiments, the *Saccharophagus degradans* strain 2-40 is grown until it reaches an $OD_{600}$ from about 0.3 to about 0.5 on the first portion of plant material. In other specific embodiments, the *Saccharophagus degradans* strain 2-40 is grown until it reaches an $OD_{600}$ from about 5 to about 10. In other specific embodiments, the *Saccharophagus degradans* strain 2-40 is grown until it reaches an $OD_{600}$ greater than 10. These embodiments of the invention are also used to make sugar by not adding yeast.

In more specific embodiments of the mixes of enzymes used to degrade a given plant material, the invention includes a composition comprising Cel5H and Cel5I. In another specific embodiment, the invention includes a composition comprising Cel5H and Cel5F.

In alternative embodiments of the mixes of enzymes used to degrade a given plant material, the invention includes a composition comprising Cel5F, Cel5H, Cel5I, Cep94A and Cep94B. In more specific embodiments, the invention includes a composition further comprising Cel6A, Bgl3C and Cel9B. In more specific embodiments, the invention includes a composition further comprising Cel5A, Cel5B, Cel5C, Cel5D, Cel5E, Cel5G, Cel5J, Cel9A, Bgl1A, Bgl1B, Ced3A and Ced3B. In additional embodiment, the composition of the invention further comprises yeast.

In alternative embodiments of the mixes of enzymes used to degrade a given plant material, the invention includes a composition comprising Cel5E, Cel5I, Cel9A, Bgl1A and Ced3B. In more specific embodiments, the invention includes a composition further comprising Cel5B, Cep94A and Cep94B. In additional embodiment, the composition of the invention further comprises yeast.

In alternative embodiments of the mixes of enzymes used to degrade a given plant material, the invention includes a composition comprising Cel5F, Cel9A, Bgl1A and Ced3B. In more specific embodiments, the invention includes a composition further comprising Cel5B, Cel5E, Cel5I, Bgl1B, Bgl3C, Cep94A and Cep94B. In additional embodiment, the composition of the invention further comprises yeast.

In alternative embodiments of the mixes of enzymes used to degrade a given plant material, the invention includes a composition comprising Cel5I, Bgl1A, Bgl1B, Ced3B and Cep94B. In more specific embodiments, the invention includes a composition further comprising Cel5A, Cel5G, Cel9A, Bgl3C and Cep94A. In additional embodiment, the composition of the invention further comprises yeast.

In alternative embodiments of the mixes of enzymes used to degrade a given plant material, the invention includes a composition comprising Cel5E, Cel5F, Cel5H, Cel6A and Cel9B. In more specific embodiments, the invention includes a composition further comprising Cel5I, Bgl3C and Cep94A. In other specific embodiments, the invention includes a composition further comprising Cel5C, Cel5D and Ced3A. In additional embodiment, the composition of the invention further comprises yeast.

In alternative embodiments of the mixes of enzymes used to degrade a given plant material, the invention includes a composition comprising Xyn10a, Xyn10b and Xyn11a. In more specific embodiments, the invention includes a composition further comprising Xyn10D and Xyn11B. In additional embodiment, the composition of the invention further comprises yeast.

DETAILED DESCRIPTION OF THE INVENTION

Figure 1:
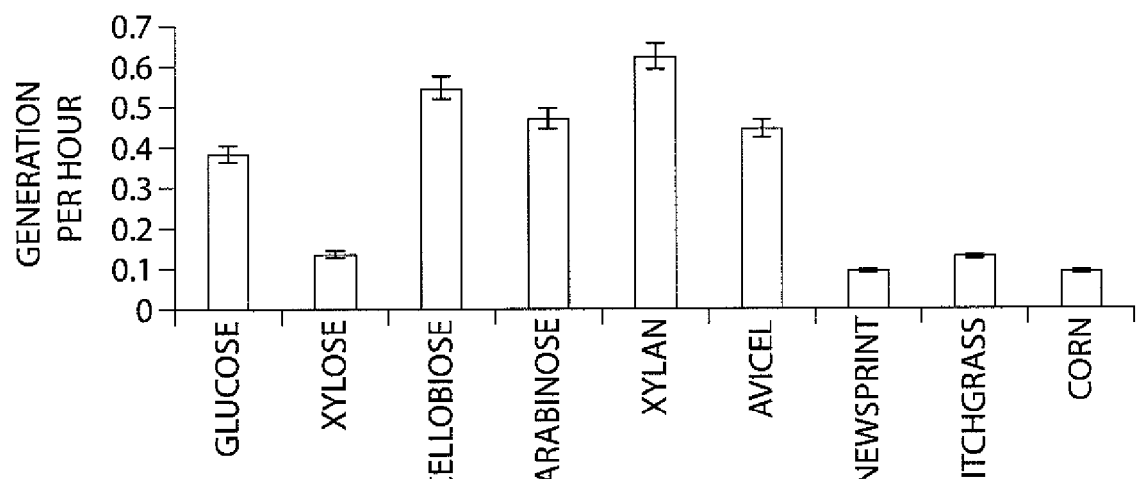
FIG. 1 is a bar graph showing the growth rate of S. degradans on different substrates.

Saccharophagus degradans 2-40 is a marine bacterium capable of degrading all of the polymers found in the higher plant cell wall using secreted and surface-associated enzymes. This bacterium has the unusual ability to saccharify whole plant material without chemical pretreatments. For example, this bacterium is able to utilize as sole carbon sources (generation time at same concentration, h): glucose (2.6), Avicel (2.25), oat spelt xylan (1.6), newsprint (>6), whole and pulverized corn leaves (>6), and pulverized *Panicum vigatum* leaves (>6), indicating the production of synergistically-acting hemicellulases, pectinases, cellulases, and possibly ligninases. Analysis of the genome sequence predicts this bacterium produces at least 12 endoglucanases, 1 cellobiohydrolase, 2 cellodextrinases, 3 cellobiases, 7 xylanases, 10 "arabinases", 5 mannases, and 14 pectinases. Analysis of zymograms and proteomic analyses of cultures revealed subsets of these enzymes are induced during growth on each of the aforementioned substrates. Induction of specific enzymes was assessed by qRT-PCR. Nomenclature for specific enzymes is explained in further detail in U.S. application Ser. No. 11/121,154, filed on May 4, 2005 and published as U.S. Publication No. 2006/0105914, which is incorporated herein in its entirety.

S. degradans effectively degrades plant material and therefore products that are constructed of plant material. Thus, the induction of the mixture of enzymes expressed in S. degradans upon exposure to a particular plant material shows that the individual enzymes and the mixture of enzymes are effective in the degradation of the plant material that the S. degradans is exposed to. This means that any two or more enzymes with increased or maintained high expression in S. degradans in response to exposure to a given plant material may be used to form an enzyme mixture for the degradation of that plant material. Two types of plant material that S. degradans is effective in degrading to simple sugars are plant material rich in cellulose and hemicellulose. Enzyme systems for degrading these two types of carbohydrates are described in greater detail below.

Cellulose

S. degradans 2-40 expresses many enzymes for the degradation of cellulose to simple sugars. For example, in the presence of corn leaves, the celluloytic enzymes shown in Table 1, below were increased.

TABLE 1

Predicted cellulases and accessory enzymes of *S. degradans* strain 2-40 and evidence supporting their identification.

| Name | Predicted function | Module(s) | MM (kDa) |
|---|---|---|---|
| Cel5A | Endo-1,4-β-glucanase (EC 3.2.1.4) | GH5/CBM6/CBM6/CBM6/GH5 | 127.2 |
| Cel5B | Endo-1,4-β-glucanase | LPB/PSL(47)/CBM6/GH5 | 60.8 |
| Cel5C | Endo-1,4-β-glucanase | LPB/PSL(47)/GH5 | 49.1 |
| Cel5D | Endo-1,4-β-glucanase | CBM2/PSL(58)/CBM10/PSL(36)/GH5 | 65.9 |
| Cel5E | Endo-1,4-β-glucanase | CBM6/CBM6/GH5 | 72.6 |
| Cel5F | Endo-1,4-β-glucanase | GH5 | 42.0 |
| Cel5G | Endo-1,4-β-glucanase | GH5/PSL(21)/CBM6/PSL(32)/Y95 | 67.9 |
| Cel5H | Endo-1,4-β-glucanase | GH5/PSL(32)/CBM6/EPR(16) | 66.9 |
| Cel5I | Endo-1,4-β-glucanase | CBM2/PSL(33)/CBM10/PSL(58)/GH5 | 77.2 |
| Cel5J | Endo-1,4-β-glucanase | GH5/CBM6/CBM6 | 65.2 |
| Cel6A | Cellobiohydrolase (EC 3.2.1.91) | CBM2/PSL(43)/CBM2/PSL(85)/GH6 | 81.9 |
| Cel9A | Endo-1,4-β-glucanase | GH9 | 62.7 |
| Cel9B | Endo-1,4-β-glucanase | GH9/PSL(54)/CBM10/PSL(50)/CBM2 | 89.5 |
| Ced3A | Cellodextrinase (EC 3.2.1.74) | LPB/GH3/PLP | 116.0 |
| Ced3B | Cellodextrinase | LPB/GH3 | 92.9 |
| Bgl1A | Cellobiase (EC 3.2.1.21) | GH1 | 52.8 |
| Bgl1B | Cellobiase | GH1 | 49.8 |
| Bgl3C | Cellobiase | LPB/GH3/UNK(511) | 95.4 |
| Cep94A | Cellobiose phosphorylase (EC 2.4.1.20) | GH94 | 91.7 |
| Cep94B | Cellodextrin phosphorylase (EC 2.4.1.49) | GH94 | 88.7 |

Figure 3:
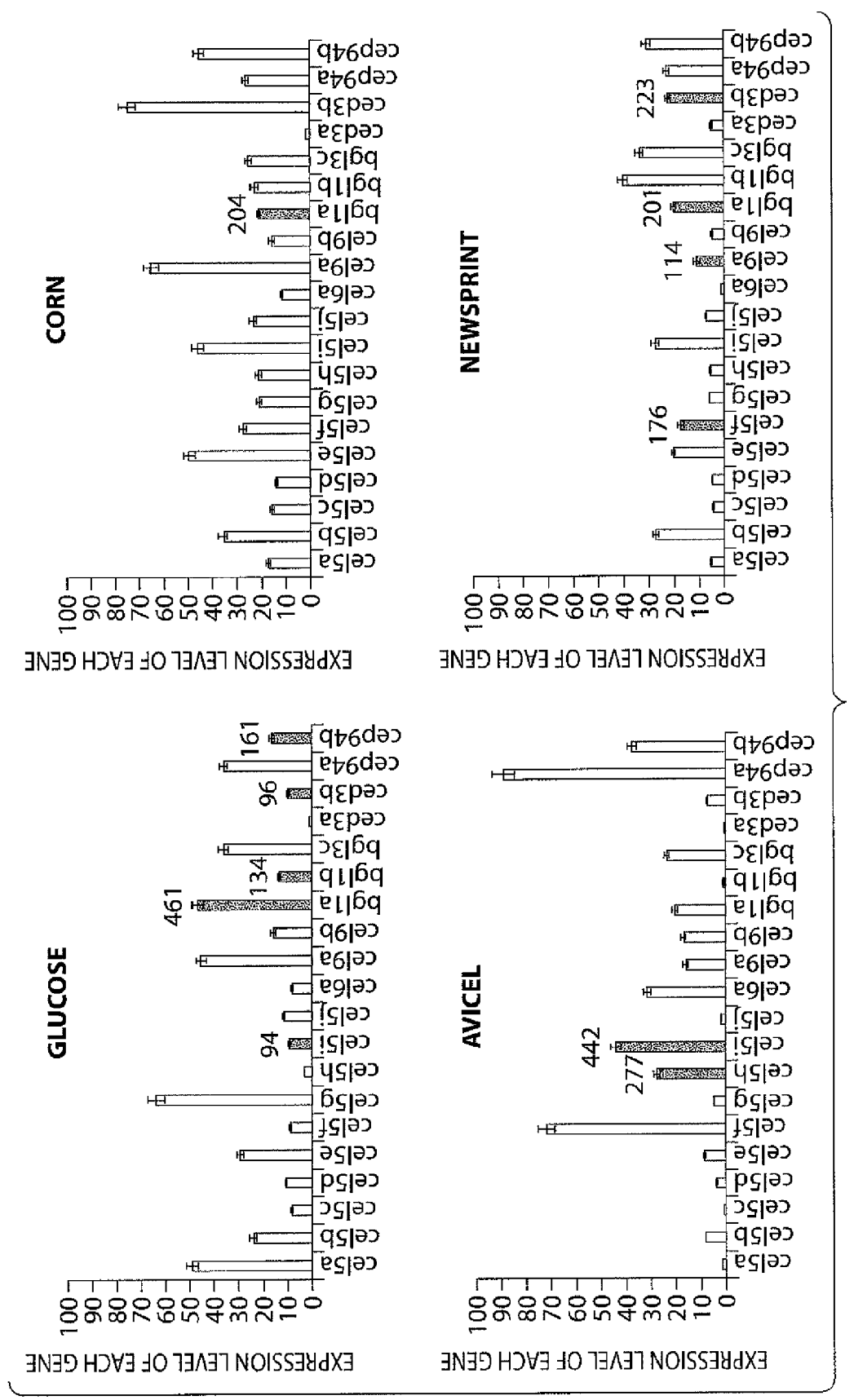
FIG. 3 shows bar graphs showing the relative expression of cellulolytic enzymes in S. degradans cultured in the presence of glucose, corn, Avicel and newsprint. Bars that are off the scale of the graphs are shown with numbers above them.

Enzymes that are increased in expression by *S. degradans* in the presence of corn leaves are likely necessary for the digestion of corn leaves to sugar. Thus, the enzymes that were increased over 20 fold, i.e. cel5F, cel5H are effective in degradation of corn leaves. Further, a mixture of all or any smaller number of the cellulolytic enzymes shown in Table 1, combined in proportion or inverse proportion to the increase of expression shown in Table 1, or the relative expression shown in FIG. 3, are used to make an enzyme mix effective for the degradation of corn leaves. Corresponding mixes are made for glucose, newsprint or Avicel, using the information shown in Table 1. Further, mixtures for other plant materials are made through the exposure of *S. degradans* to the plant material and detection of the expression of degradation enzymes through detecting the RNA, protein or activity levels of the degradation enzymes.

Moreover, the following enzymes were induced as shown below in Table 2 in *S. degradans* when exposed to Avicel, microcrystalline cellulose in a chemically pure form, for 10 hours.

TABLE 2

Fold increase in enzymes after 10 hours growth of *S. degradans* strain 2-40 on Avicel.

| Basal Expression | Fold Increase after 10 h Growth on Avicel | | |
|---|---|---|---|
| | Low (<5) | Medium (5-25) | High (>25) |
| Low (<1% GK) | | cel5C<br>cel5D<br>ced3A | cel5E<br>cel5F<br>cel5H<br>cel6A<br>cel9B |
| Medium (2-10%) | cel5A<br>cel5G | cel5B<br>cel5J<br>cel9A<br>ced3B | cel5I<br>bgl3C<br>cep94A |
| High (>10%) | bgl1A<br>bgl1B | cep94B | |

It appears that cel5A, cel5G, cel9A, cel5B, ced3B, bgl1A and cep94B are constituitively expressed in *S. degradans*

2-40. After 2 hours of growth on Avicel, cel9A expression increases. This is followed by an increase in cel5F expression at 4 hours, and increases in cel5H and cel5I expression at 10 hours. Cel5I continues to be overexpressed even at 24 hours of culture on Avicel.

Figure 4:
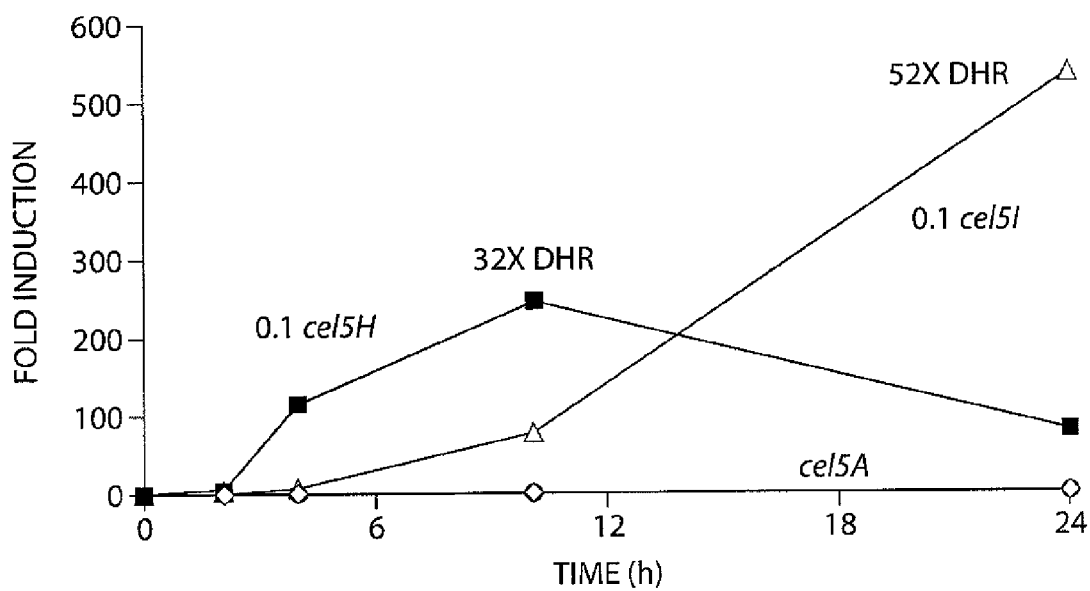
FIG. 4 is a line graph showing the fold induction of cel5A, cel5H and cel5I in Saccharophagus degradans strain 2-40 when grown on cellulose over time.
Figure 5:
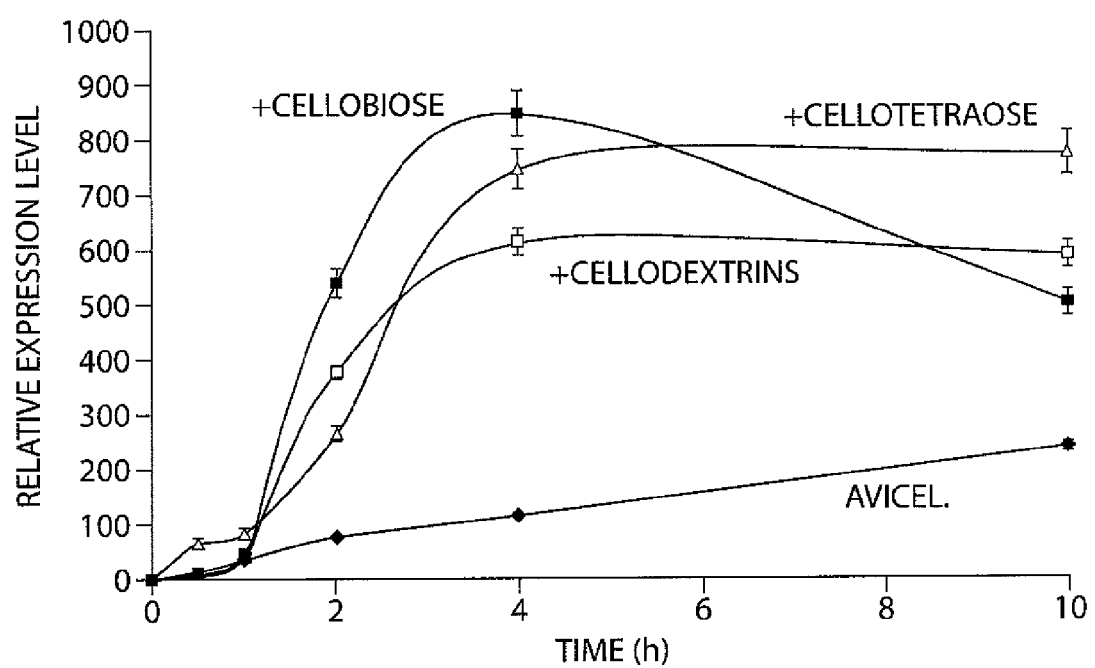
FIG. 5 is a line graph showing the relative expression level of cel5H in Saccharophagus degradans strain 2-40 when grown in the presence of cellodextrins, cellobiose, cellotraose and avicel.

It has also been shown that Cel5I and Cel5H are particularly important for the degradation of cellulose. Cel5I is induced over 500 fold and cel5H over 100 fold when *S. degradans* 2-40 is exposed to cellulose (FIG. 4). Moreover, cel5H is expressed over 500 fold when *S. degradans* 2-40 is exposed to cellodextrins, such as cellobiose, cellotraose and cellodextrin (FIG. 5). Thus, either of these proteins could be used to efficiently break down cellulose to simple sugars.

Further, degradation enzymes with higher expression in *S. degradans* when exposed to a particular plant material, may be constitutively and/or over-expressed in an engineered bacterium, thus making a bacterium that is effective in the degradation of the particular plant material. For example, mixtures of proteins that are shown to be induced in *S. degradans* in the presence of corn leaves in Table 1, could be introduced into a bacteria so that they are constitutively expressed. These proteins could also be introduced so they are expressed at a high rate. These engineered bacteria are then used to degrade plant material, in this example, corn leaves. In one embodiment the bacterium to be engineered is *S. degradans*. In another embodiment, the bacterium to be engineered in *E. coli*.

Hemicellulose

*S. degradans* 2-40 expresses many enzymes for the degradation of hemicellulose to simple sugars. Hemicellulose exists as short branched chains of sugar monomers. Sugars that make up hemicellulose include xylose, mannose, galactose, and/or arabinose. Hemicellulose forms a series of crosslinks with cellulose and pectin to form a rigid cell wall. Unlike cellulose, hemicellulose is mostly amorphous, relatively weak and susceptible to hydrolization.

Figure 6:
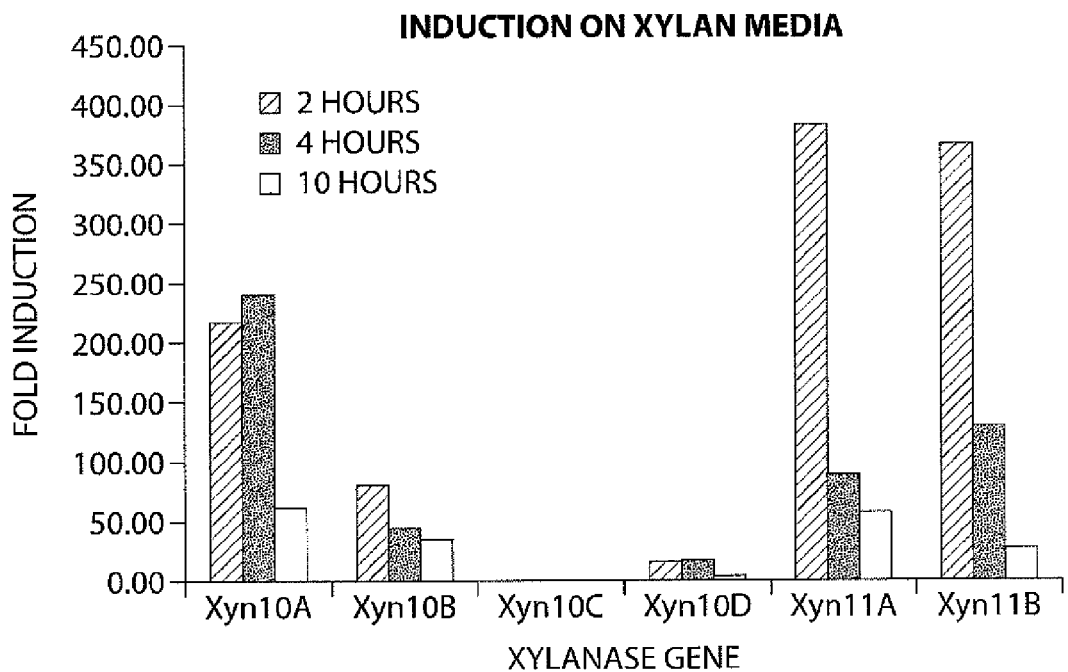
FIG. 6 is a bar graph showing the fold induction of hemicellullytic enzymes in S. degradans cultured in the presence of xylan.
Figure 7:
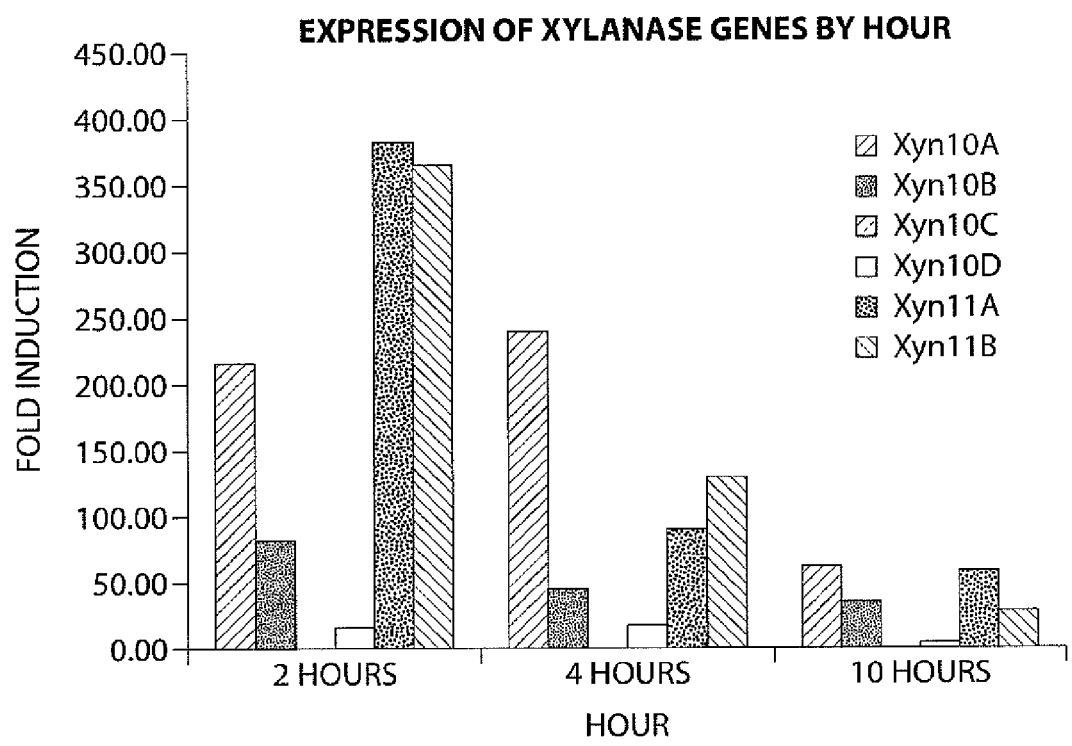
FIG. 7 is a bar graph showing the fold induction of hemicellullytic enzymes in S. degradans cultured for various times in the presence of xylan.

*S. degradans* produces many hemicellulases that are used to break down hemicellulose to simpler sugars. As shown in FIG. 6, expression of xyn10A, xyn10B, xyn10D, xyn11A and xyn11B is omduced in *S. degradans* 2-40 grown on xylan, containing hemicellulose. Moreover, as shown in FIG. 7, expression of xyn10A, xyn10B, xyn10D, xyn11A and xyn11B was shown after 10 hours of culture of *S. degradans* 2-40 on xylan. However, at 2 hours, the greatest increases in expression were for xyn11A and xyn11B, while the greatest increases in expression at 4 hours of culture of *S. degradans* 2-40 on xylan was xyn10A.

Thus, Xyn10a, Xyn10b, Xyn10d, Xyn11a And Xyn11b are all important for hemicellulose break down to simpler sugars. However, particular emphasis should be placed on the importance of Xyn10a, Xyn10b, Xyn11a And Xyn11b.

Cloning and Expression of *S. degradans* Proteins in *E. coli*

The basic cloning and expression system uses pET28B (Novagen) as the vector, *E. coli* DH5a (invitrogen) as the cloning strain, and *E. coli* BL-21 (DE3) ROSETTA™ cells (Novagen) for protein expression strain. This system allows the cloning of toxic or otherwise difficult genes because the vector places expression under the control of a T7 lac promoter—which is lacking in the cloning strain DH5α, thereby abolishing even low-level expression during plasmid screening and propagation. After the blue/white screen, plasmids are purified from DH5α and transformed into the expression host. The ROSETTA™ strain has the T7 lac promoter, allowing IPTG-inducible expression of the vector-coded protein and lacks the Lon and Omp proteases.

The nucleotide sequences of gene models were obtained from the DOE JGI's *S. degradans* genome web server and entered into the PRIMERQUEST™ design tool. The design parameters were Optimum $T_m$ 60° C., Optimum Primer Size 20 nt, Optimum GC %=50, and the product size ranges were chosen so that the primers were selected within the first and last 100 nucleotides of each ORF in order to clone as much of the gene as reasonably possible. The cloning and expression vector, pET28B, provides a C-terminal 6× Histidine fusion as well as the start and stop codon for protein expression. Thus, careful attention to the frame of the vector and insert sequences is required when adding 5' restriction sites to the PCR primers. The resulting "tailed primers" were between 26 to 30 nt long, and their sequences were verified by "virtual cloning" analysis using the PDRAW software package. This program allows vector and insert DNA sequences to be cut with standard restriction enzymes and ligated together. The amino acid translations of the resulting sequences were examined to detect any frame shifts introduced by errors in primer design. Following this verification, the primers were purchased from Invitrogen (Frederick, Md.).

PCR reactions contained 10 pMol of forward and reverse primers, 1 µl of 10 mM DNTPs, 1.5 µl of 100 mM $MgCl_2$, and 1 µl PROOF PRO® Pfu Polymerase in a 50 µl reaction with 0.5 µl of 2-40 genomic DNA as the template. PCRs conditions used standard parameters for tailed primers and Pfu DNA polymerase. PCR products were cleaned up with the QIAGEN QIAquick PCR Cleanup kit and viewed in 0.8% agarose gels. Following cleanup and confirmation of size, PCR products and pET28B are digested with appropriate restriction enzymes, usually AscI and ClaI at 37° C. for 1 to 4 hours, cleaned up using the QIAquick kit, and visualized in agarose gels. Clean digestions are ligated using T4 DNA ligase for at least 2 hours in the dark at room temperature. Ligations are then transformed into *E. coli* DH5α by electroporation. Transformants are incubated one hour at 37° C. in non-selective media, and then plated onto LB agar containing ampicillin and X-gal. As pET28B carries an Ampr gene and inserts are cloned into the lacZ ORF, white colonies contain the insert sequence. White colonies are picked with toothpicks and patched onto a new LB/Amp/X-gal plate, with three of the patched colonies also being used to inoculate 3 ml overnight broths. Plasmids are prepped from broths which correspond to patched colonies which remained white after overnight outgrowth. These plasmid preps are then singly digested with an appropriate restriction enzyme and visualized by agarose electrophoresis for size confirmation.

The plasmids are then heat-shock transformed into the ROSETTA™ strain. The transformants are incubated 1 hour at 37° C. in non-selective rescue medium, plated on LB agar with Amp and Cm (ROSETTA™ medium) and incubated overnight at 37° C. Any colonies thus selected should contain the vector and insert. This is confirmed by patching three colonies onto a ROSETTA™ medium plate and inoculating corresponding 3 ml overnight broths. The next morning the broths are used to inoculate 25 ml broths which are grown to an $OD_{600}$ of around 0.6 (2-3 hours). At this point a 1 ml aliquot is removed from the culture, pelleted and resuspended in 1/10 volume 1×SDS-PAGE treatment buffer. This pre-induced sample is frozen at −20° C. for later use in Western blots. The remaining broth is then amended to 1 mM IPTG and incubated 4 hours at 37° C. Induced pellet samples are collected at hourly intervals. These samples and the pre-induced control are run in standard SDS-PAGE gels and electroblotted onto PVDF membrane or nitrocellulose. The membranes are then processed as western blots using a 1/5000 dilution of monoclonal mouse α-HISTAG® primary antibodies followed by HRP-conjugated goat α-mouse IgG secondary antibodies. Bands are visualized colorimetrically using BioRad's Opti-4CN substrate kit. Presence of His tagged bands in the induced samples, but not in uninduced controls, confirms successful expression and comparison of bands from the hourly time points are used to optimize induction parameters in later, larger-scale purifications.

Production and Purification of Recombinant Proteins

Expression strains are grown to an $OD_{600}$ of 0.6 to 0.8 in 500 ml or 1 liter broths of ROSETTA™ medium. At this point a non-induced sample is collected and the remaining culture induced by addition of 100 mM IPTG to a final concentration of 1 mM. Induction is carried out for four hours at 37° C. or for 16 hours at 25° C. Culture pellets are harvested and frozen overnight at −20° C. for storage and to aid cell lysis. Pellets are then thawed on ice for 10 minutes and transferred to pre-weighed falcon tubes and weighed. The cells are then rocked for 1 hour at 25° C. in 4 ml of lysis buffer (8M Urea, 100 mM $NaH_2PO_4$, 25 mM Tris, pH 8.0) per gram wet pellet weight. The lysates are centrifuged for 30 minutes at 15,000 g to pellet cell debris. The cleared lysate (supernatant) is pipetted into a clean falcon tube, where 1 ml of QIAGEN 50% Nickel-NTA resin is added for each 4 ml cleared lysate. This mixture is gently agitated for 1 hour at room temperature to facilitate binding between the $Ni^{+2}$ ions on the resin and the His tags of the recombinant protein. After binding, the slurry is loaded into a disposable mini column and the flow through (depleted lysate) is collected and saved for later evaluation. The resin is washed twice with lysis buffer that has been adjusted to pH 7.0; the volume of each of these washes is equal to the original volume of cleared lysate. The flow through of these two washes is also saved for later analysis in western blots to evaluate purification efficiency.

At this point the columns contain relatively purified recombinant proteins which are immobilized by the His tags at their C-terminus. This is an ideal situation for refolding, so the column is moved to a 4° C. room and a series of renaturation buffers with decreasing urea concentrations are passed through the column. The renaturation buffers contain varying amounts of urea in 25 mM Tris pH 7.4, 500 mM NaCl, and 20% glycerol. This buffer is prepared as stock solutions containing 6M, 4M, 2M and 1M urea. Aliquots of these can be easily mixed to obtain 5M and 3M urea concentrations thus providing a descending series of urea concentrations in 1M steps. One volume (the original lysate volume) of 6M buffer is passed through the column, followed by one volume of 5M buffer, continuing on to the 1M buffer—which is repeated once to ensure equilibration of the column at 1M urea. At this point the refolded proteins are eluted in 8 fractions of ⅒th original volume using 1M urea, 25 mM Tris pH 7.4, 500 mM NaCl, 20% glycerol containing 250 mM imidazole. The imidazole disrupts the Nickel ion-His tag interaction, thereby releasing the protein from the column.

Western blots are used to evaluate the amount of His tagged protein in the depleted lysate, the two washes, and the eluted fractions. If there is an abundance of recombinant protein in the depleted lysate and/or washes it is possible to repeat the process and "scavenge" more protein. Eluate fractions that contain the protein of interest are pooled and then concentrated and exchanged into storage buffer (20 mM Tris pH 7.4, 10 mM NaCl, 10% glycerol) using centricon centrifugal ultrafiltration devices (Millipore). The enzyme preparations are then aliquoted and frozen at −80° C. for use in activity assays.

EXAMPLES

The following examples further support, but do not exclusively represent, preferred embodiments of the present invention.

Zymogram Protocol

All activity gels were prepared as standard SDS-PAGE gels with the appropriate CP substrate incorporated directly into the separating gel. Zymograms are cast with 8% polyacrylamide concentration and the substrate dissolved in dH$_2$O and/or gel buffer solution to give a final concentration of 0.1% (HE-cellulose), 0.15% (barley β-glucan), or 0.2% (xylan). Gels are run under discontinuous conditions according to the procedure of Laemmli with the exception of an 8 minute treatment at 95° C. in sample buffer containing a final concentration of 2% SDS and 100 mM dithiothreitol (DTT). After electrophoresis, gels are incubated at room temperature for 1 hour in 80 ml of a renaturing buffer of 20 mM PIPES buffer pH 6.8 which contains 2.5% Triton X-100, 2 mM DTT and 2.5 mM CaCl$_2$. The calcium was included to assist the refolding of potential calcium-binding domains such as the tsp3s of Lam16A.

After the 1 hour equilibration, gels were placed in a fresh 80 ml portion of renaturing buffer and held overnight at 4° C. with gentle rocking. The next morning gels were equilibrated in 80 ml of 20 mM PIPES pH 6.8 for 1 hour at room temperature, transferred to a clean container, covered with the minimal amount of PIPES buffer and incubated at 37° C. for 4 hours. Following incubation gels were stained for 30 minutes with a solution of either 0.25% Congo red in dH$_2$O (HE-cellulose, β-glucan and xylan) or 0.01% Toluidine blue in 7% acetic acid. Gels were destained with 1M NaCl for Congo red and dH$_2$O for Toluidine blue until clear bands were visible against a stained background.

Example 1

Genotyping Methods

The growth rate of *S. degradans* was cultured on different substrates (FIG. 1). The basic media was composed of (2.3% Instant Ocean, 0.05% Yeast Extract, 0.05% NH$_4$Cl, 15 mM Tris, pH 6.8). The final concentration of each carbon source were 0.2% for Glucose, Xylose, *Cellobiose, Arabinose, Xylan, Avicel* and 1.0% for Newsprint, Switchgrass, and corn leaves. *S. degradans* grew on all plant material it was grown on.

Figure 2:
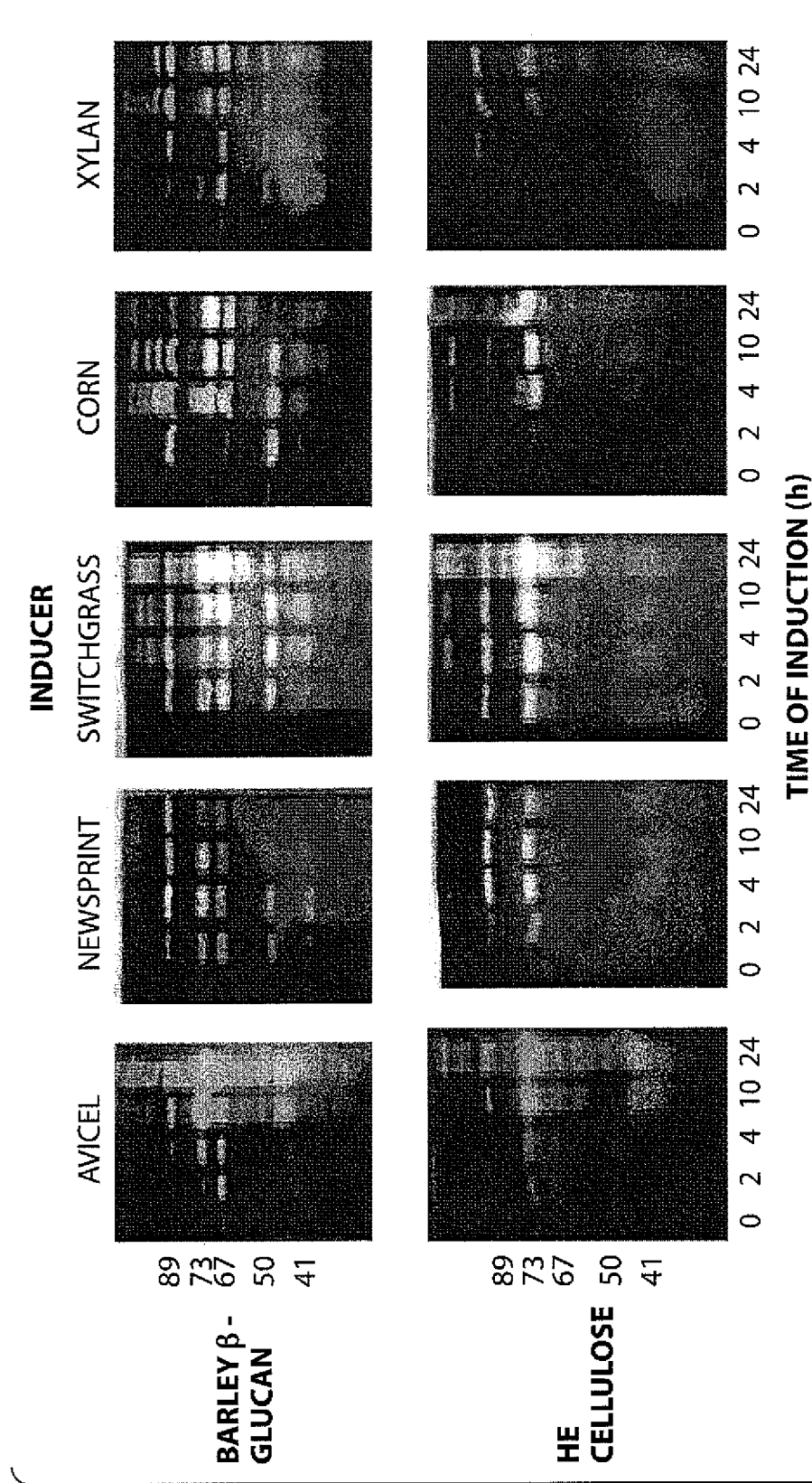
FIG. 2 shows Congo Red stained SDS gels of proteins from S. degradans grown on either 0.1% barley β-glucan or HE cellulose.

A Zymogram was performed to find which glucanases were induced during growth on various cell wall polymers (FIG. 2). Cells were grown to an OD$_{600}$ of 0.3-0.5 in media containing glucose as the sole carbon source, harvested and transferred to the same volume of media containing the indicated inducer. Samples were removed at the indicated times and proteins in samples normalized to OD$_{600}$ were fractionated by standard SDS-PAGE in which either 0.1% barley α-glucan or HE cellulose was included in the resolving gel. Gels were incubated in refolding buffer (20 mM PIPES [piperazine-N,N'-bis(2-ethanesulfonic acid)] buffer [pH 6.8], 2.5% Triton X-100, 2 mM dithiothreitol, 2.5 mM CaCl$_2$) for 1 h at room temperature and then held overnight in fresh refolding buffer at 4° C. The gels were transferred to PIPES buffer, incubated at 37° C., and stained in 0.25% Congo red. Calculated masses are shown on the left in kDa. Different glucanases were expressed in the presence of different plant materials or carbohydrate sources used.

The expression of cellulolytic enzymes during growth on glucose and cell wall polymers was determined (FIG. 3). *S. degradans* was cultured on glucose to OD$_{600}$ 0.3-0.4, harvested and transferred to the same volume medium containing the indicated substrate. After 10 hours the RNA was isolated using the RNA PROTECT™ Bacteria Reagent (Qiagen) and RNEASY™ Mini kit (Qiagen). The cDNA was synthesized using the QIANTITECT™ Reverse Transcription Kit. The 120-200 bp fragments of each indicated gene or two control genes for Guanylate kinase and Dihydrofolate reductase were amplified using the SYBR Green™ master mix kit (Roche) and a LIGHT CYCLER™ 480 (Roche). The bars shown with numbers above them are presented at ⅒ scale. Different celluloytic enzymes were induced by different plant materials or carbohydrate sources.

Example 2

Measurement of Increase in Expression of Xyn10A, Xyn10B, Xyn11A and Xyn11B in Response to Growth of *S. degradans* on Xylan Primers were designed for six target genes: xyn10A-D and xyn11A-B along with two house keeping genes: dihydrofolate reductase and guanylate kinase. *S. degradans* was cultured in glucose media until OD$_{600}$ reached 0.370-0.400. The 0 hour time point was taken and the cultures were transferred to xylan media for 10 hour time course experiments. A second culture was transferred back to glucose as a control. Samples were taken at 0, 2, 4 and 10 hours from both the xylan and glucose cultures.

RNA from each sample was purified using RNAprotect™ bacteria reagent (Qiagen) and Rneasy MiniKit. The isolated mRNA was transformed using QuantiTech™ reverse transcriptase and expression patterns were analyzed using Light-Cycler Pro™ pRT-PCR.

As shown in FIG. 6, xyn10A, xyn10B, xyn10D, xyn11A and xyn11B all had greater mRNA expression at 2, 4, and 10 hours after exposure to xylan. The increases were the greatest for xyn10A, xyn10B, xyn11A and xyn11B. As shown in FIG. 7, the highest fold induction of mRNA expression at 2 hours of culture of *S. degradans* on xylan, was for xyn11A and xyn11B. Xyn110A had the highest induction at 4 hours. At 10 hours, xyn10A, xyn10B, xyn11A and xyn11B all had higher fold induction.

As *S. degradans* increases expression of these proteins when it is exposed to xylan, and with the sequence homology these proteins have to known hemicellulase genes, Xyn10A, Xyn10B, Xyn10D, Xyn11A and Xyn11B are functional hemicellulases that can be used to break down hemicellulose.

EQUIVALENTS AND INCORPORATION BY REFERENCE

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

The instant application includes numerous citations to learned texts, published articles and patent applications as well as issued U.S. and foreign patents. The entire contents of all of these citations are hereby incorporated by reference herein.

The invention claimed is:

1. An isolated *Saccharophagus degradans* prokaryotic cell-free composition comprising *Saccharophagus degradans* lysate, said lysate comprising Cel5F, wherein the composition is effective in the degradation of plant material and wherein the *Saccharophagus degradans* is grown to an $OD_{600}$ of at least 0.3 in the presence of the plant material prior to lysis.

2. The *Saccharophagus degradans* prokaryotic cell-free composition of claim 1, wherein the lysate further comprises Cel5H.

3. The *Saccharophagus degradans* prokaryotic cell-free composition of claim 1, wherein the lysate further comprises Cel5I and Cep94A.

4. The *Saccharophagus degradans* prokaryotic cell-free composition of claim 3, wherein the lysate further comprises Cel6A, Bgl3C and Cel9B.

5. The *Saccharophagus degradans* prokaryotic cell-free composition of claim 4, wherein the lysate further comprises Cel5A, Cel5B, Cel5C, Cel5D, Cel5E, Cel5G, Cel5J, Cel9A, Bgl1A, Bgl1B, Ced3A, Cep94B and Ced3B.

6. An isolated *Saccharophagus degradans* prokaryotic cell-free composition comprising *Saccharophagus degradans* lysate, said lysate comprising Cel5F, Cel9A, Bgl1A and Ced3B, wherein the composition is effective in the degradation of plant material, and
    wherein the *Saccharophagus degradans* is grown to an $OD_{600}$ of at least 0.3 in the presence of plant material prior to lysis.

7. The *Saccharophagus degradans* prokaryotic cell-free composition of claim 6, wherein the lysate further comprises Cel5B, Cel5E, Cel5I, Bgl1B, Bgl3C, Cep94A and Cep94B.

8. An isolated *Saccharophagus degradans* prokaryotic cell-free composition comprising *Saccharophagus degradans* lysate, said lysate comprising Cel5E, Cel5F, Cel5H, Cel6A and Cel9B, wherein the composition is effective in the degradation of plant material, and
    wherein the *Saccharophagus degradans* is grown to an $OD_{600}$ of at least 0.3 in the presence of plant material prior to lysis.

9. The *Saccharophagus degradans* prokaryotic cell-free composition of claim 8, wherein the lysate further comprises Cel5I, Bgl3C and Cep94A.

10. The *Saccharophagus degradans* prokaryotic cell-free composition of claim 8, wherein the lysate further comprises Cel5C, Cel5D and Ced3A.

11. The *Saccharophagus degradans* prokaryotic cell-free composition of any one of claim 1, 6 or 8, wherein the *Saccharophagus degradans* is grown to a $OD_{600}$ of from 0.3 to 10 in the presence of the plant material prior to lysis.

12. The *Saccharophagus degradans* prokaryotic cell-free composition of any one of claim 1, 6 or 8, wherein the *Saccharophagus degradans* is grown to a $OD_{600}$ of at least 0.370 in the presence of the plant material prior to lysis.

13. The *Saccharophagus degradans* prokaryotic cell-free composition of claim 12, wherein the *Saccharophagus degradans* is grown to a $OD_{600}$ of from 0.370 to 0.400 in the presence of the plant material prior to lysis.

* * * * *

UNITED STATES PATENT AND TRADEMARK OFFICE
CERTIFICATE OF CORRECTION

| | |
|---|---|
| PATENT NO. | : 9,057,081 B2 |
| APPLICATION NO. | : 12/112776 |
| DATED | : June 16, 2015 |
| INVENTOR(S) | : Steven Hutcheson et al. |

It is certified that error appears in the above-identified patent and that said Letters Patent is hereby corrected as shown below:

On the Title Page, Column 1, Item (73), correct the name of the Assignee by replacing:

"Aemetis Technologies, Inc., Cupertino, CA (US)" with --University of Maryland, College Park, Maryland (US)--.

Signed and Sealed this
Twenty-ninth Day of December, 2015

Michelle K. Lee
*Director of the United States Patent and Trademark Office*